(12) United States Patent
Neff et al.

(10) Patent No.: US 11,324,494 B2
(45) Date of Patent: May 10, 2022

(54) DEVICE AND METHOD FOR CUTTING-TO-LENGTH SURGICAL SUTURE MATERIAL

(71) Applicant: Harro Hoefliger Verpackungsmaschinen GmbH, Allmersbach im Tal (DE)

(72) Inventors: Ingmar Neff, Allmersbach im Tal (DE); Siegfried Weber, Allmersbach im Tal (DE)

(73) Assignee: Harro Hoefliger Verpackungsmaschinen GmbH, Allmersbach im Tal (DE)

( * ) Notice: Subject to any disclaimer, the term of this patent is extended or adjusted under 35 U.S.C. 154(b) by 327 days.

(21) Appl. No.: 16/394,124

(22) Filed: Apr. 25, 2019

(65) Prior Publication Data

US 2019/0343511 A1 Nov. 14, 2019

(30) Foreign Application Priority Data

May 8, 2018 (EP) .................................... 18171314

(51) Int. Cl.
*A61B 17/04* (2006.01)
*B65H 54/71* (2006.01)
(Continued)

(52) U.S. Cl.
CPC ......... *A61B 17/0467* (2013.01); *B65H 54/71* (2013.01); *A61B 17/06004* (2013.01);
(Continued)

(58) Field of Classification Search
CPC .......... A61B 17/0467; A61B 17/06004; A61B 17/06166; A61B 2090/061; A61B 2017/00526; B65H 54/71; Y10T 29/49929
See application file for complete search history.

(56) References Cited

U.S. PATENT DOCUMENTS 3,875,946 A 4/1975 Duncan
4,799,311 A 1/1989 Matsutani
(Continued)

FOREIGN PATENT DOCUMENTS

CH 681 272 A5 2/1993
CN 105745371 A 7/2016
(Continued)

OTHER PUBLICATIONS

European Search Report dated Nov. 14, 2018 in European Application No. 18 17 1314.0, with English translation of the relevant parts.
(Continued)

*Primary Examiner* — Katherine H Schwiker
(74) *Attorney, Agent, or Firm* — Collard & Roe, P.C.

(57) ABSTRACT

A device and method for cutting-to-length surgical suture material uses a thread spool having a continuous thread of the surgical suture material, a thread advancing gripper for drawing off a defined length of surgical suture material, and a cutting unit for cutting the surgical suture material. By way of a deflection installation, the surgical suture material is placeable so as to be angled to the primary transport direction in at least one open loop. The length of the open loop can be variably adjusted. The cutting unit is positioned between the thread spool and the deflection installation.

2 Claims, 3 Drawing Sheets

(51) Int. Cl.
*A61B 17/06* (2006.01)
*A61B 17/00* (2006.01)

(52) U.S. Cl.
CPC ............... *A61B 17/06166* (2013.01); *A61B 2017/00526* (2013.01)

(56) References Cited

U.S. PATENT DOCUMENTS

| | | | |
|---|---|---|---|
| 4,922,904 A * | 5/1990 | Uetake | A61B 17/06004 163/1 |
| 6,076,255 A | 6/2000 | Shikakubo et al. | |
| 6,226,336 B1 | 5/2001 | Atarius et al. | |
| 6,263,558 B1 | 7/2001 | Blanch et al. | |
| 6,520,184 B2 | 2/2003 | Bonnassieux | |
| 9,949,736 B2 | 4/2018 | Kim | |
| 2018/0193017 A1 * | 7/2018 | Lenihan | A61B 17/06004 |

FOREIGN PATENT DOCUMENTS

| | | |
|---|---|---|
| DE | 100 20 602 A1 | 12/2000 |
| EP | 0 663 187 A2 | 7/1995 |
| EP | 0 910 994 A1 | 4/1999 |
| EP | 2 245 991 A1 | 11/2010 |
| GB | 2 221 414 A | 2/1990 |
| KR | 10-1581865 B1 | 12/2015 |

OTHER PUBLICATIONS

Chinese Office Action in Chinese Application No. 201910377630.3 dated Jan. 26, 2022.

* cited by examiner

DEVICE AND METHOD FOR CUTTING-TO-LENGTH SURGICAL SUTURE MATERIAL

CROSS REFERENCE TO RELATED APPLICATIONS

Applicant claims priority under 35 U.S.C. § 119 of European Application No. 18 171 314.0 filed May 8, 2018, the disclosure of which is incorporated by reference.

BACKGROUND OF THE INVENTION

1. Field of the Invention

The invention relates to a device and to a method for cutting-to-length surgical suture material so as to position the beginning of a thread from surgical suture material in a reproducible manner and to render said thread to a defined cut-off length in a flexible manner. A continuous thread of surgical suture material can thus be shortened to a desired length by means of such a device. The surgical suture material herein can be fastened to a surgical needle or else be present as a loose thread.

2. Description of the Related Art

Devices for cutting-to-length surgical suture material are known. Said devices typically have a thread spool having a continuous thread of surgical suture material. The desired length of surgical suture material is drawn off from the thread spool by means of a thread advancing gripper that is guided in a linear manner in a (horizontal or vertical) transport direction. This drawing-off from the thread spool is in part controlled by way of a so-called dancer mechanism. The surgical suture material is subsequently cut by means of a cutting unit at the desired location.

The leading thread end of the surgical suture material typically has to be advanced to a fixed position, since the connection of the leading thread end to the surgical needle can be performed exclusively at this defined position. Adapting said joining position to dissimilar thread lengths is impossible in terms of machine technology. Therefore, the maximum possible length of surgical suture material is typically always present as a free thread length. Adapting the device to dissimilar thread lengths in this instance is performed by a displacement of the cutting unit in the longitudinal direction of the free thread. Accordingly, the repositioning range of the thread advancing gripper is also adapted with a view to the start position of the latter. Depending on the position of the cutting unit, the surgical suture material is then cut at a specific spacing from the thread spool. Cutting machines of this type therefore have a correspondingly long construction length. Moreover, the free thread length is comparatively large such that significant vibrations can arise in the region of the unwound surgical suture material. This can impede both the threading of the thread into the needle, as well as the actual cutting of the thread.

SUMMARY OF THE INVENTION

Proceeding from said known prior art, the invention is based on the object of specifying an improved device for cutting-to-length surgical suture material to dissimilar thread lengths, said device enabling an ideally compact construction mode.

These and other objects are accomplished by a device for cutting surgical suture material according to one aspect of the invention and by a method according to another aspect of the invention. Expedient refinements of the invention are discussed below.

The device according to the invention for cutting surgical suture material possesses a thread spool having a continuous thread of the surgical suture material as well as a thread advancing gripper for drawing off a defined length of surgical suture material. Moreover, a cutting unit for cutting the surgical suture material is present. According to the invention, a deflection installation by way of which the surgical suture material can be placed along a secondary axis so as to be angled to the primary transport direction in at least one open loop is provided. The length of said open loop herein can be variably adjusted. The cutting unit herein is positioned between the deflection installation and the thread spool for the continuous thread.

On account of the presence of the deflection installation it is no longer necessary for the cutting unit to be configured so as to be displaceable in the longitudinal direction. Rather, the deflection installation enables dissimilar lengths of surgical suture material to be unwound and to be cut off. The dissimilar lengths herein are determined by the length of the open loop. Therefore, the free thread length of the surgical suture material does also no longer have to correspond to the maximum possible thread length, but now only to the minimum thread length required. In this way, the device can be reduced to approximately one third of the length required to date. The device according to the invention can therefore be constructed so as to be significantly shorter and thus also significantly more compact.

The surgical suture material by way of the deflection installation can preferably be placed so as to be perpendicular to the primary transport direction in at least one open loop. Sufficient space is typically available perpendicularly to the longitudinal axis of the unwound thread, such that such an open loop can be configured within the device according to the invention. The open loop can therefore be integrated in the device in an optimal manner, such that said device can be constructed so as to be compact.

In one embodiment which in terms of construction is particularly preferable, the deflection installation can have a front and a rear deflection unit, each being configured so as to be stationary. One or a plurality of repositionable compensation rollers can be present between the two stationary deflection units. The at least one compensation roller, by way of the length of the repositioning path thereof, herein determines the loop length of the surgical suture material. The repositioning path of the compensation roller can in particular be entered at a control unit such that an adjustment of the desired thread length is possible in a simple and precise manner in the case of the device according to the invention.

Because no drawing-off of surgical suture material is performed by way of the front deflection unit, the front deflection unit can preferably be configured as a stationary thread deflection. By contrast, further surgical suture material is drawn off by way of the rear deflection unit as soon as the compensation roller is repositioned from the initial position of the latter. In order for gentle drawing-off of the surgical suture material to be enabled, the rear deflection unit can therefore preferably be configured as a stationary deflection roller.

The deflection installation in one advantageous embodiment can be configured so as to be height-adjustable. Since the cutting-off of the surgical suture material when viewed in the transport direction always takes place behind the deflection installation, the thread advancing gripper must pass the location of the deflection installation in order for the new leading thread end to be transported to the front again. When the deflection installation is configured so as to be height-adjustable the individual components of the deflection installation can yield towards the top or towards the bottom so as to make space for the thread advancing gripper. The thread advancing gripper, on account thereof, can be more rapidly repositioned, in particular on the path to the new leading thread end; moreover, the thread of the surgical suture material is treated with care, on account thereof.

Alternatively or additionally thereto, the thread advancing gripper when moving back without transporting the surgical suture material and/or when moving forward while transporting the surgical suture material, can describe an arc about the deflection installation. The thread advancing gripper could thus bypass the deflection installation so as to be lateral to or above the latter, for example.

In the case of the method according to the invention for cutting-to-length surgical suture material, the surgical suture material by means of a thread advancing gripper is first drawn off from a thread spool having a continuous thread. The thread advancing gripper moves forward to a predetermined terminal position. The surgical suture material by way of a deflection installation is subsequently placed in at least one open loop that runs so as to be angled to the primary transport direction of the drawn-off surgical suture material. On account thereof, further surgical suture material is drawn off from the thread spool without the thread advancing gripper moving any further. The surgical suture material drawn off from the thread spool is subsequently cut off by a cutting unit. The cutting unit herein is positioned between the thread spool and the deflection installation.

The cutting unit is preferably situated close to the deflection installation. On account thereof, the trailing thread end, after the severing of the continuous thread, can drop downwards through the deflection installation and does not completely remain on the deflection installation. This facilitates the onward transport of the cut-to-length thread pieces.

On account of the method according to the invention, the repositioning path of the thread advancing gripper is always identical, independently of the length of the actually cut-off surgical suture material. The repositioning path can be chosen so as to be relatively short so that said repositioning step requires correspondingly little time. While further surgical suture material is drawn off by the deflection installation, the leading thread end is present so as to be already positionally fixed, so that further processing steps can be performed at the leading thread end. The thread advancing gripper can thus move up to a joining location for connecting the surgical suture material to a corresponding needle, for example. In this case, fixing of the leading end of the surgical suture material in the needle can already be performed during the further drawing-off of the surgical suture material. On account of the unwinding of the surgical suture material being performed in parallel with operational processes at the leading positioned thread end, the thread length thus now only has a minimum influence on the actual processing time. Moreover, a longer processing time is available for the actual thread transport by way of the thread advancing gripper on account of the parallel implementation. The surgical suture material can thus be transported more slowly by the thread advancing gripper and thus with greater care for the suture material.

BRIEF DESCRIPTION OF THE DRAWING

Other objects and features of the invention will become apparent from the following detailed description considered in connection with the accompanying drawings. It is to be understood, however, that the drawings are designed as an illustration only and not as a definition of the limits of the invention.

In the drawings.

DETAILED DESCRIPTION OF PREFERRED EMBODIMENTS

Figure 1:
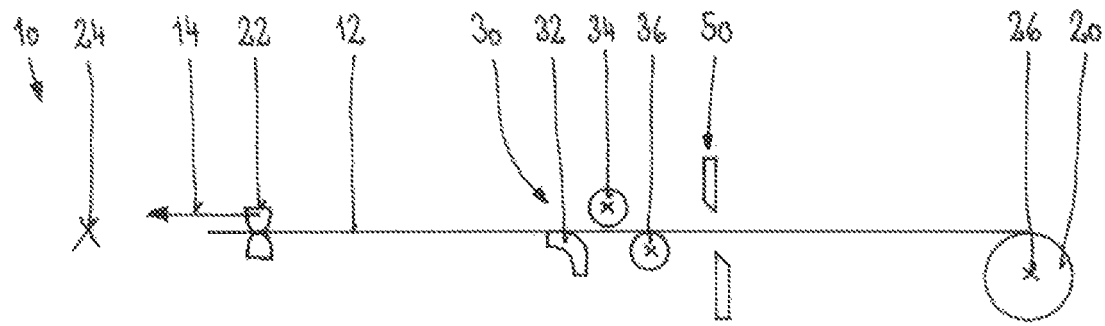
FIG. 1 shows a schematic lateral view of a first embodiment of the invention, in which the deflection installation is situated in the initial position thereof.
Figure 2:
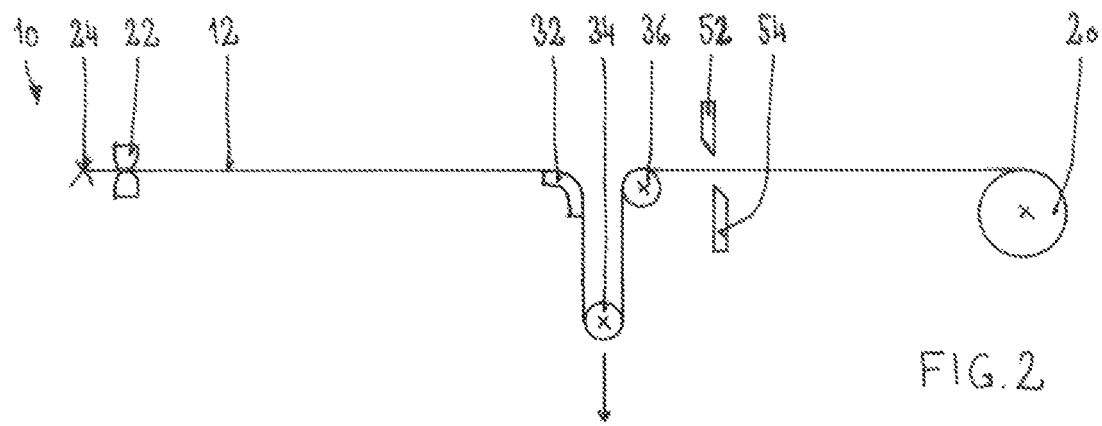
FIG. 2 shows a schematic lateral view according to FIG. 1 during the repositioning of the deflection installation.
Figure 3:
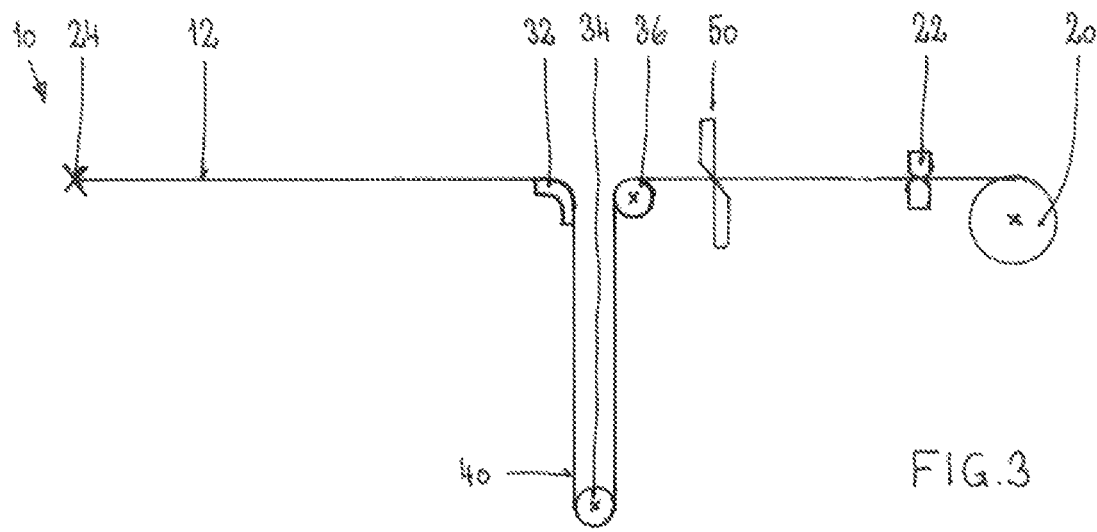
FIG. 3 shows a schematic lateral view according to FIG. 2, in which the deflection installation is situated in the terminal position thereof, immediately prior to the cutting of the surgical suture material.
Figure 4:
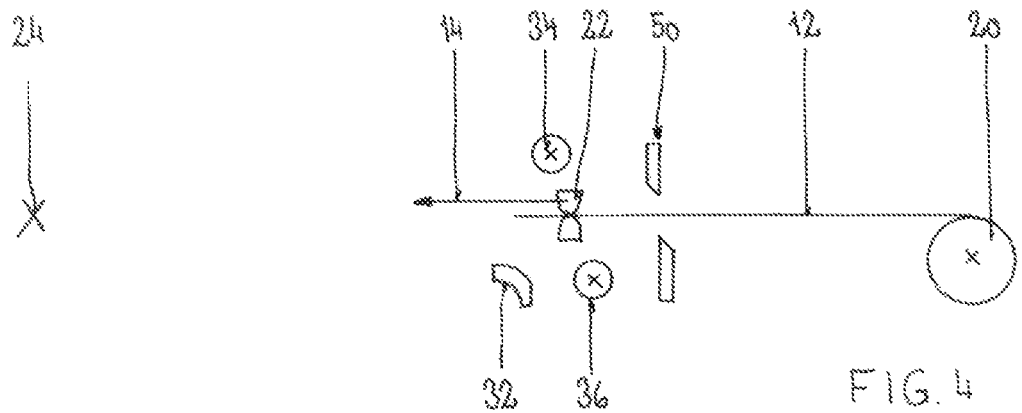
FIG. 4 shows a schematic lateral view of the device according to FIGS. 1 to 3, having a height-adjustable deflection installation during the advancing of the thread.

A first embodiment of the device 10 according to the invention for cutting-to-length surgical suture material 12 is schematically illustrated in FIGS. 1 to 3. The device 10 possesses a thread spool 20 having a continuous thread of the surgical suture material 12. The surgical suture material 12 by means of a thread advancing gripper 22 can be drawn off from said thread spool 20. To this end, the thread advancing gripper 22 moves forward to a defined terminal position 24. The thread spool 20 herein rotates about the axis 26 thereof, and the surgical suture material 12 in the present exemplary case is unwound in the horizontal direction (primary transport direction 14).

In the present exemplary case, connecting the leading end of the surgical suture material 12 to a needle is performed at the terminal position 24. To this end, the leading end of the surgical suture material 12 is introduced somewhat into the hollow end of the needle. The hollow end of the needle is subsequently compressed so as to fix the surgical suture material 12 in the needle. Since the leading end of the surgical suture material 12 no longer has to be moved once the terminal position 24 has been reached, the procedure of fastening the surgical suture material 12 in the needle can be started immediately upon reaching the terminal position 24.

A deflection installation 30 is present between the thread spool 20 and the terminal position 24. The deflection installation 30 in the present exemplary embodiment possesses a stationary thread deflection 32. An individually repositionable compensation roller 34 is present in the advancing direction behind the stationary thread deflection 32. A stationary deflection roller 36 is disposed therebehind. The surgical suture material 12 is guided above the stationary thread deflection 32 and the stationary deflection roller 36; by contrast, the surgical suture material 12 is situated below the repositionable compensation roller 34. Once the terminal position 24 has been reached, further surgical suture material 12 can be drawn off from the thread roller 20 by repositioning the compensation roller 34 (see FIG. 2). On account thereof, a comparatively long piece of surgical suture material 12 can be cut off without having to further reposition the thread advancing gripper 22.

The surgical suture material 12, on account of the repositioning of the compensation roller 34, is placed in an approximately U-shaped open loop 40. The length of the loop 40 herein is determined by the repositioning distance of the compensation roller 34. Said repositioning distance can be individually entered at a control unit of the device 10. On account thereof, the overall length of the cut-off surgical suture material 12 can be varied and adapted to dissimilar requirements in a simple manner.

Once the compensation roller 34 has reached the desired terminal position thereof (see FIG. 3), the cutting of the surgical suture material 12 can be performed. To this end, a cutting unit 50 is disposed between the deflection installation 30 and the thread spool 20. The cutting unit 50 in the present exemplary case possesses an upper cutting blade 52 and a lower cutting blade 54. The cutting unit 50 is aligned so as to be stationary, since an adaptation of the thread length of the surgical suture material 12 can be performed by the deflection installation 30. This simplifies the constructive complexity of the cutting unit 50 and thus also of the device 10.

In principle, alternative cutting units 50 are also possible. The cutting unit can thus have a single cutting blade, for example, which can be disposed laterally of the surgical suture material 12. On account of the tension in the thread, a single cutting blade can be sufficient in order to guarantee a clean and accurate cut. The construction mode of the cutting unit in this context is in principle irrelevant to the invention.

Before the surgical suture material 12 is cut, the trailing thread end of the surgical suture material 12 has to be held again by means of the thread advancing gripper 22. To this end, the thread advancing gripper 22, after fixing the leading end of the surgical suture material 12 in the needle, is moved back again to the initial position of said thread advancing gripper 22 behind the cutting unit 50 (see FIG. 3). Should the leading end of the surgical suture material 12 not have to be fixed in a needle, a second rear thread gripper can also be used for fixing the leading thread end of the subsequent surgical suture material 12. Said rear thread gripper can be provided so as to be stationary directly behind the cutting unit 50. After the cutting of the thread, the actual thread advancing gripper 22 can then release the leading thread end and move back so as to acquire the subsequent leading thread end from the rear thread gripper.

Figure 5:
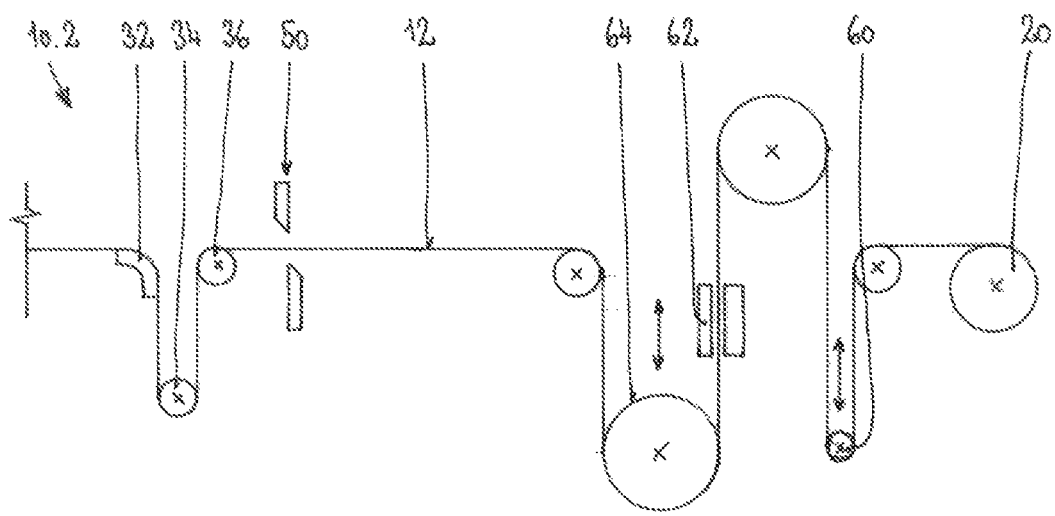
FIG. 5 shows a schematic lateral view of a second embodiment of the invention, immediately prior to the cutting of the surgical suture material.

The drawing-off of the surgical suture material 12 is typically performed by means of a dancer mechanism 60. A second embodiment of the device 10.2 according to the invention having such a dancer mechanism 60 for drawing-off the surgical suture material 12 from a thread spool 20 is schematically illustrated in FIG. 5. The dancer mechanism 60 is configured so as to be height-adjustable, and in the case of a stationary thread advancing gripper can be repositioned in order for additional surgical suture material 12 to be drawn off from the thread spool 20. When the thread advancing gripper having the leading thread end is then repositioned, the dancer mechanism 60 is successively moved back again to the initial position thereof, so as to release the correspondingly required thread length. To this end, the dancer mechanism 60 is typically disposed between the cutting unit 50 and the thread spool 20 having the continuous thread; in the ideal case, the dancer mechanism 60 is situated in the direct proximity of the thread spool 20.

In order to prevent that the leading thread end of the surgical suture material 12 frays after cutting, the surgical suture material 12 at the later cutting location can be welded by means of a heating element 62. The heating element 62 herein is disposed between the dancer mechanism 60 and the cutting unit 50. In principle, the surgical suture material is not welded across the entire thread length but only at the later cutting location. To this end, an integer multiple of the desired thread length of the surgical suture material 12 must run between the cutting unit 50 and the heating element 62. The heating element 62 was therefore typically configured so as to be adjustable, like the cutting unit 50. By contrast, in the embodiment of the device 10.2 according to the invention, illustrated in FIG. 5, a repositionable deflection roller 64 by way of which an equalization of the thread length can be performed is configured between the heating element 62 and the cutting unit. In this way, the heating element 62 can be configured so as to be stationary.

Figure 6:
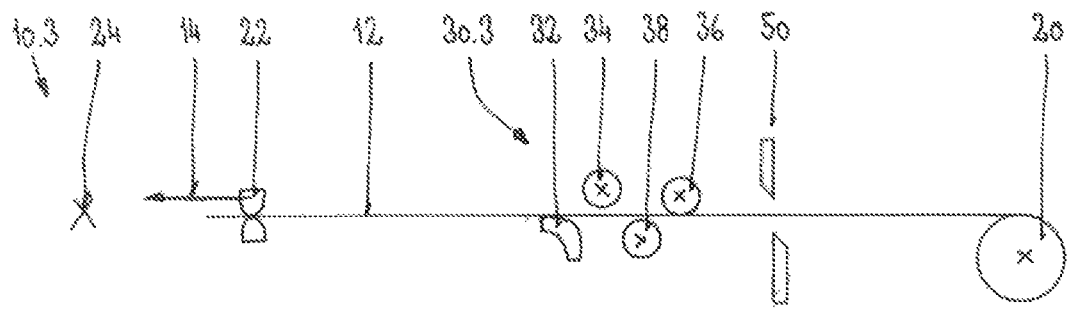
FIG. 6 shows a schematic lateral view of a third embodiment of the invention, in which the deflection installation is situated in the initial position thereof.
Figure 7:
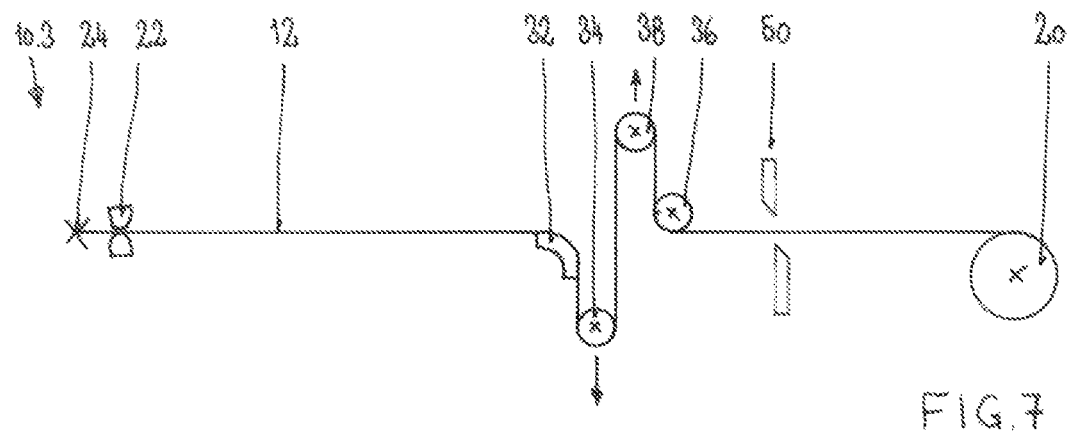
FIG. 7 shows a schematic lateral view according to FIG. 6 during the repositioning of the deflection installation.
Figure 8:
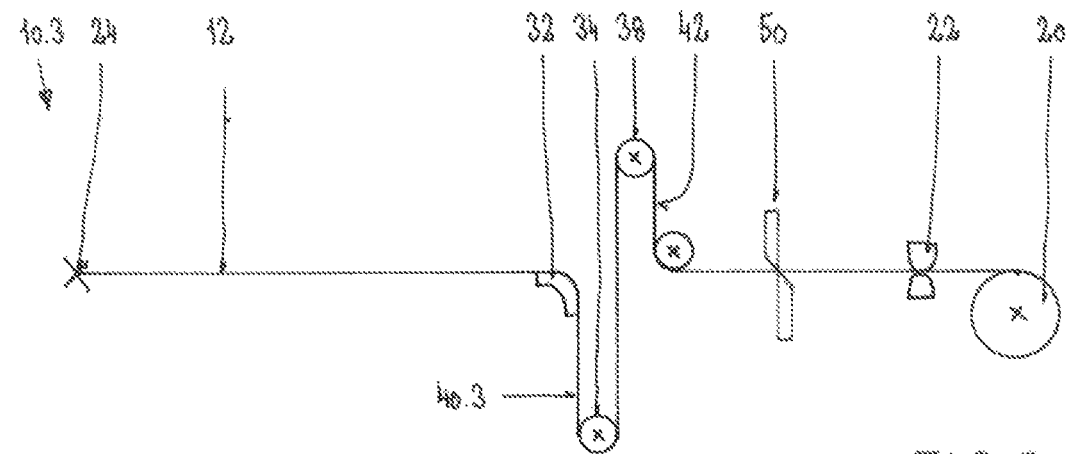
FIG. 8 shows a schematic lateral view according to FIG. 7, in which the deflection installation is situated in the terminal position thereof, immediately prior to the cutting of the surgical suture material.

A third embodiment of the device 10.3 according to the invention for cutting-to-length surgical suture material 12 is schematically illustrated in FIGS. 6 to 8. The device 10.3, like the device 10, possesses a thread spool 20 having an continuous thread of the surgical suture material 12, as well as a thread advancing gripper 22.

A deflection installation 30.3 is present between the thread spool 20 and the terminal position 24. The deflection installation 30.3 in the present exemplary embodiment possesses a stationary thread deflection 32. A first repositionable compensation roller 34 as well as a second repositionable compensation roller 38 are present in the advancing direction behind the stationary thread deflection 32. A stationary deflection roller 36 is disposed therebehind. The surgical suture material 12 is guided above the stationary thread deflection 32 and the second compensation roller 36; by contrast, the surgical suture material 12 is situated below the first repositionable compensation roller 34 as well as the stationary deflection roller 36. Once the terminal position 24 has been reached, further surgical suture material 12 can be drawn off from the thread spool 20 by repositioning the two compensation rollers 34, 38 (see FIG. 7). On account thereof, a comparatively long piece of surgical suture material 12 can be cut off without the thread advancing gripper 22 having to be further repositioned.

The two compensation rollers 34, 38 herein can be simultaneously repositioned, as is illustrated in FIGS. 7 and 8. Alternatively thereto, it would also be possible for only one of the two compensation rollers 34, 38 to be repositioned first. The repositioning of the other compensation roller 34, 38 would commence only once the maximum repositioning path of said compensation roller 34, 38 has been reached.

The surgical suture material 12, on account of the repositioning of the compensation rollers 34, 38, is placed in two open loops 40.3, 42. The length of the two open loops 40.3, 42 herein is determined by the repositioning distance of the corresponding compensation roller 34, 38. On account thereof, the overall length of the cut-off surgical suture material 12 can be varied and adapted to dissimilar requirements in a simple manner.

Although only a few embodiments of the present invention have been shown and described, it is to be understood that many changes and modifications may be made thereunto without departing from the spirit and scope of the invention.

What is claimed is:

1. A method for cutting-to-length surgical suture material, comprising the following method steps:
   drawing off, using a thread advancing gripper, the surgical suture material from a thread spool having a continuous thread;
   moving the thread advancing gripper forward to a predetermined terminal position, the predetermined terminal position comprising a joining location for connecting the surgical suture material to a needle;
   subsequently placing the surgical suture material by way of a deflection installation positioned between the thread spool and the predetermined terminal position in at least one open loop that runs so as to be angled to a the primary transport direction of the drawn-off surgical suture material;
   fixing a leading end of the surgical suture material in the needle while repositioning the deflection installation, and
   subsequently cutting off the surgical suture material drawn off from the thread spool using a cutting unit.

2. The method according to claim 1, wherein the length of the at least one open loop is variably adjustable.

* * * * *